US008434163B1

(12) United States Patent
Nudo

(10) Patent No.: US 8,434,163 B1
(45) Date of Patent: May 7, 2013

(54) VEST SYSTEM THAT PROVIDES FOR A TARGETED HEAT/COOL THERAPY TREATMENT

(76) Inventor: Carmen L. Nudo, Elwood, IL (US)

( * ) Notice: Subject to any disclaimer, the term of this patent is extended or adjusted under 35 U.S.C. 154(b) by 115 days.

(21) Appl. No.: 12/977,750

(22) Filed: Dec. 23, 2010

(51) Int. Cl.
A41D 1/04 (2006.01)
(52) U.S. Cl.
USPC .................... 2/102; 2/16; 2/22; 2/170; 2/247; 2/250
(58) Field of Classification Search ............. 2/102, 108, 2/93, 94, 92, 115, 247
See application file for complete search history.

(56) References Cited

U.S. PATENT DOCUMENTS

| 262,577 | A | * | 8/1882 | Day ..................................... 2/94 |
| 1,520,962 | A | * | 12/1924 | North ................................. 2/102 |
| 2,403,676 | A | * | 7/1946 | Modlinski ............................ 2/94 |
| 3,802,215 | A | * | 4/1974 | Rowe ............................ 62/259.3 |
| 4,601,067 | A | * | 7/1986 | Buonassissi ....................... 2/102 |
| 5,031,244 | A | * | 7/1991 | Inagaki .............................. 2/102 |
| 5,038,779 | A | * | 8/1991 | Barry et al. .................... 607/108 |
| 5,146,625 | A | * | 9/1992 | Steele et al. ....................... 2/102 |
| 5,148,804 | A | * | 9/1992 | Hill et al. ....................... 607/108 |
| 5,265,782 | A | * | 11/1993 | McNamara .......................... 2/94 |
| 5,302,806 | A |   | 4/1994 | Simmons et al. |
| 5,361,412 | A | * | 11/1994 | Perry .................................. 2/69 |
| 5,692,238 | A | * | 12/1997 | Watson, Jr. ........................ 2/102 |
| D391,038 | S |   | 2/1998 | Thompson |
| 5,787,505 | A | * | 8/1998 | Piwko et al. ...................... 2/115 |
| 5,826,273 | A | * | 10/1998 | Eckes .................................. 2/69 |
| D421,329 | S | * | 3/2000 | Adams ........................... D2/841 |
| 7,022,093 | B2 |   | 4/2006 | Smith et al. |
| 7,090,624 | B1 | * | 8/2006 | Chrishon ...................... 482/105 |
| D625,376 | S | * | 10/2010 | Marabellas .................. D21/791 |
| 8,105,371 | B1 | * | 1/2012 | Giocondo, Jr. ................ 607/108 |
| 2004/0010836 | A1 |   | 1/2004 | Audi |
| 2006/0036304 | A1 |   | 2/2006 | Cordani et al. |
| 2006/0253954 | A1 | * | 11/2006 | Music ............................... 2/115 |
| 2007/0256206 | A1 | * | 11/2007 | Nilsen ................................ 2/69 |
| 2009/0139005 | A1 | * | 6/2009 | Whaley .............................. 2/69 |
| 2009/0217440 | A1 | * | 9/2009 | Sutker .............................. 2/114 |

* cited by examiner

Primary Examiner — Khoa Huynh
Assistant Examiner — Brieanna Fuller

(57) ABSTRACT

The present invention features a therapy vest system for providing targeted heat or cold application to a person. In some embodiments, the vest of the vest system comprises a first shoulder pocket secured over a first shoulder region of the vest, and also a second shoulder pocket secured over a second shoulder region of the vest. In some embodiments, the vest further comprises a first side pocket secured to a first rib side region of the vest and also a second side pocket secured to a second rib side region of the vest. In some embodiments, the vest system further comprise extremity tubes.

1 Claim, 6 Drawing Sheets (In Use View)

(Front View)

(Back View)

(Side View)

(ISO View)

(Cross-sectional View)

(In Use View)

VEST SYSTEM THAT PROVIDES FOR A TARGETED HEAT/COOL THERAPY TREATMENT

BACKGROUND OF THE INVENTION

The present invention features an invention that provides for a targeted heat/cool therapy treatment on a person. The invention is a vest comprising pockets at specific locations for insertion of a heating or cooling pack therein. More specifically, the present invention comprises a shoulder pocket on the vest, along with pockets at other important regions.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
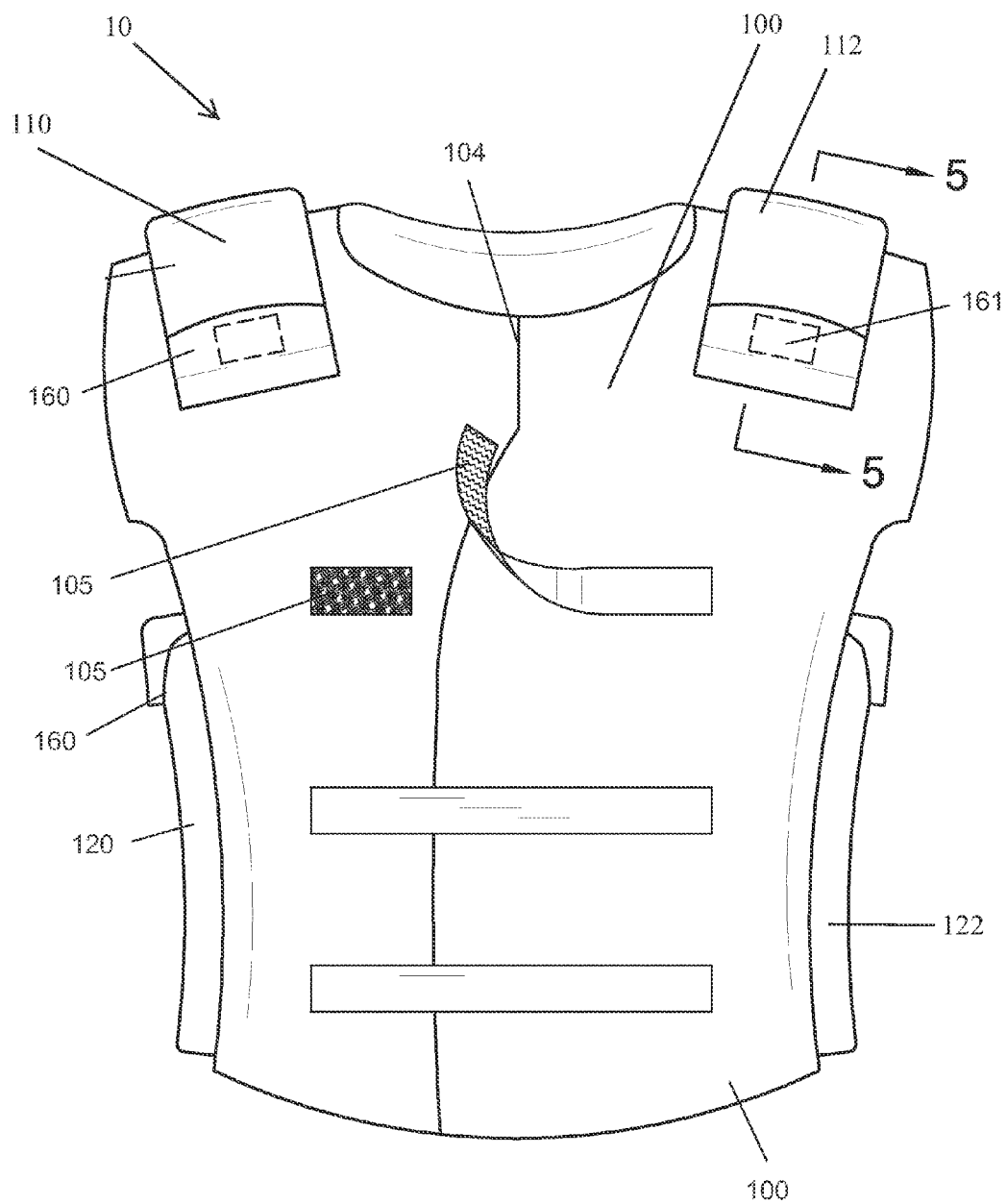
FIG. 1 shows a front side of the vest, with the first and second shoulder pockets, and first and second side pockets secured to the vest. In some embodiments, the vest can be closed up with a hook-and-loop mechanism.
Figure 2:
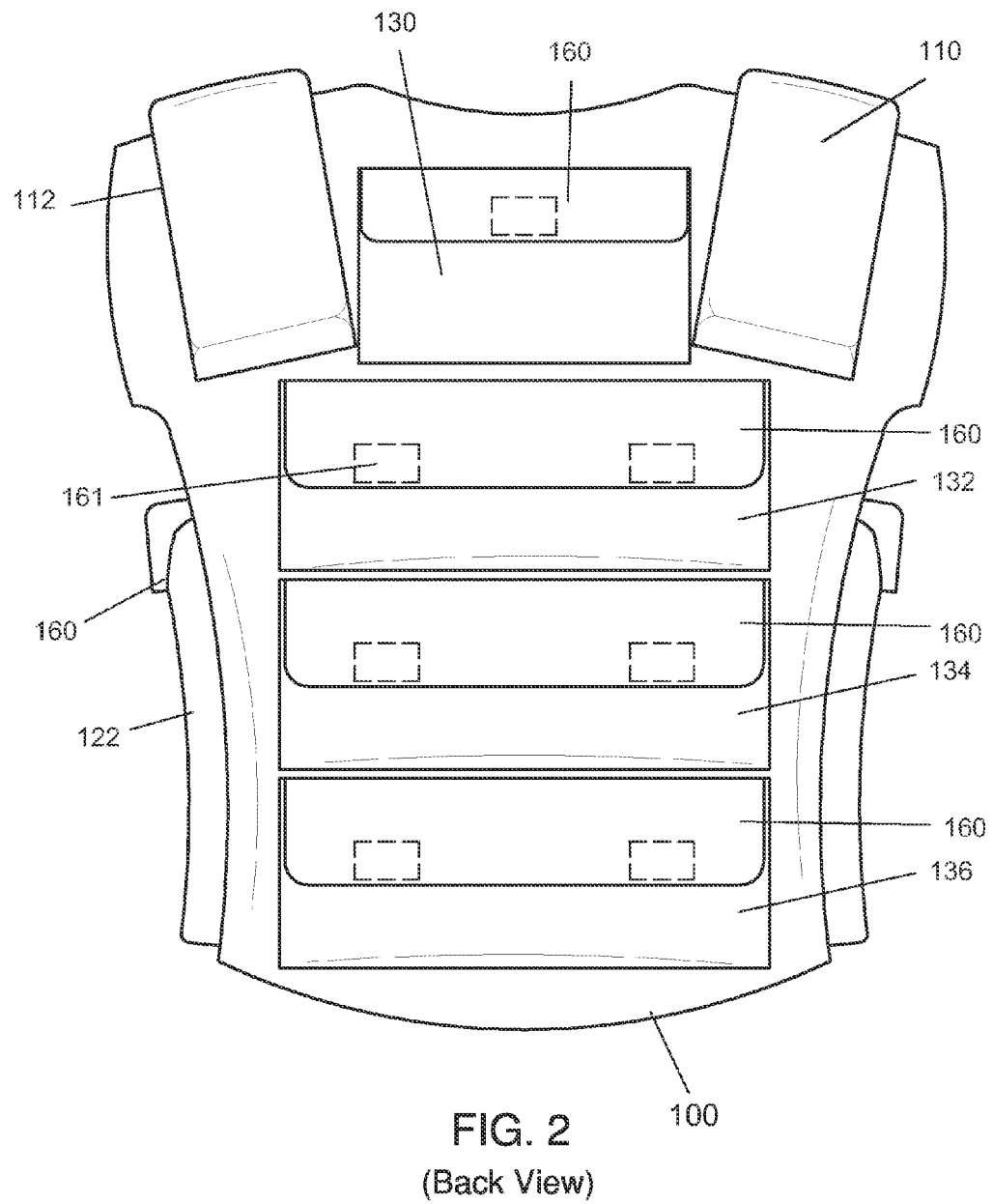
FIG. 2 shows a back side of the vest, with the first and second shoulder pockets, and first and second side pockets secured to the vest. Additional pockets are also secured to the back of the vest.
Figure 3:
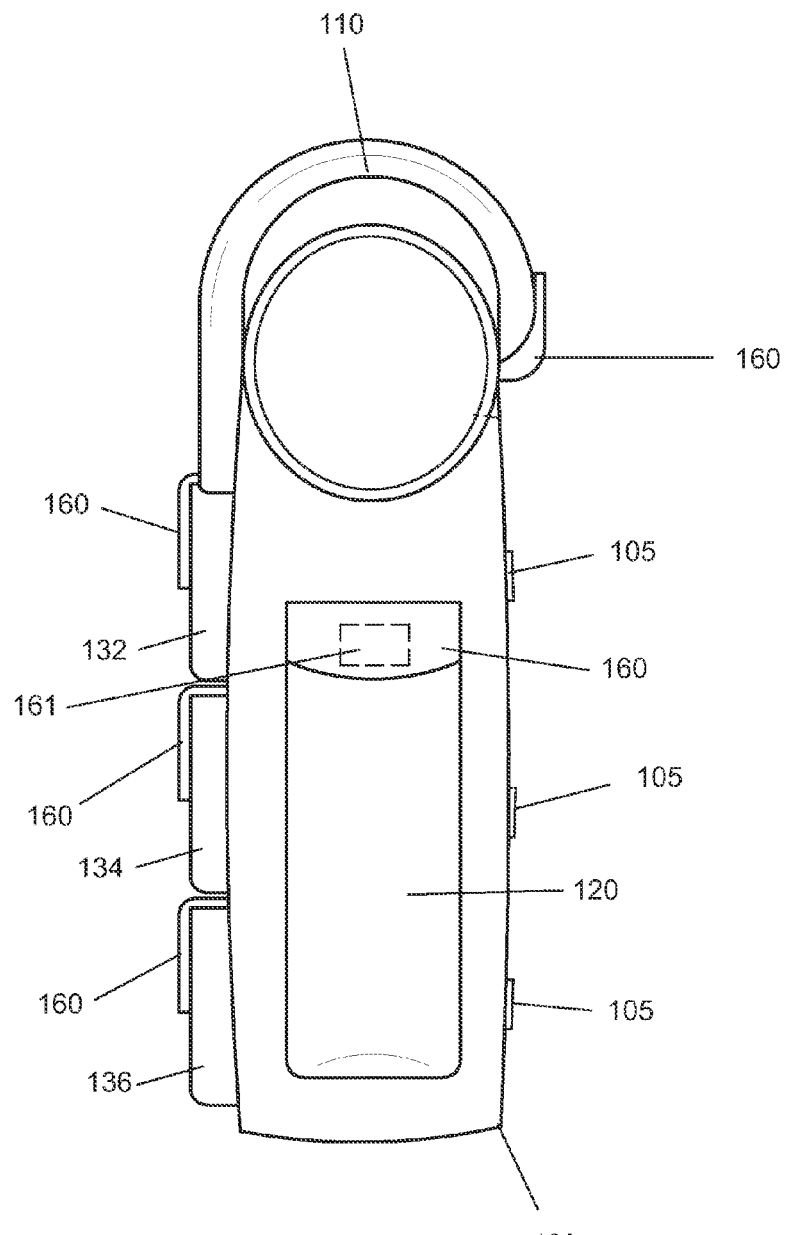
FIG. 3 shows a side view of the vest.
Figure 4:
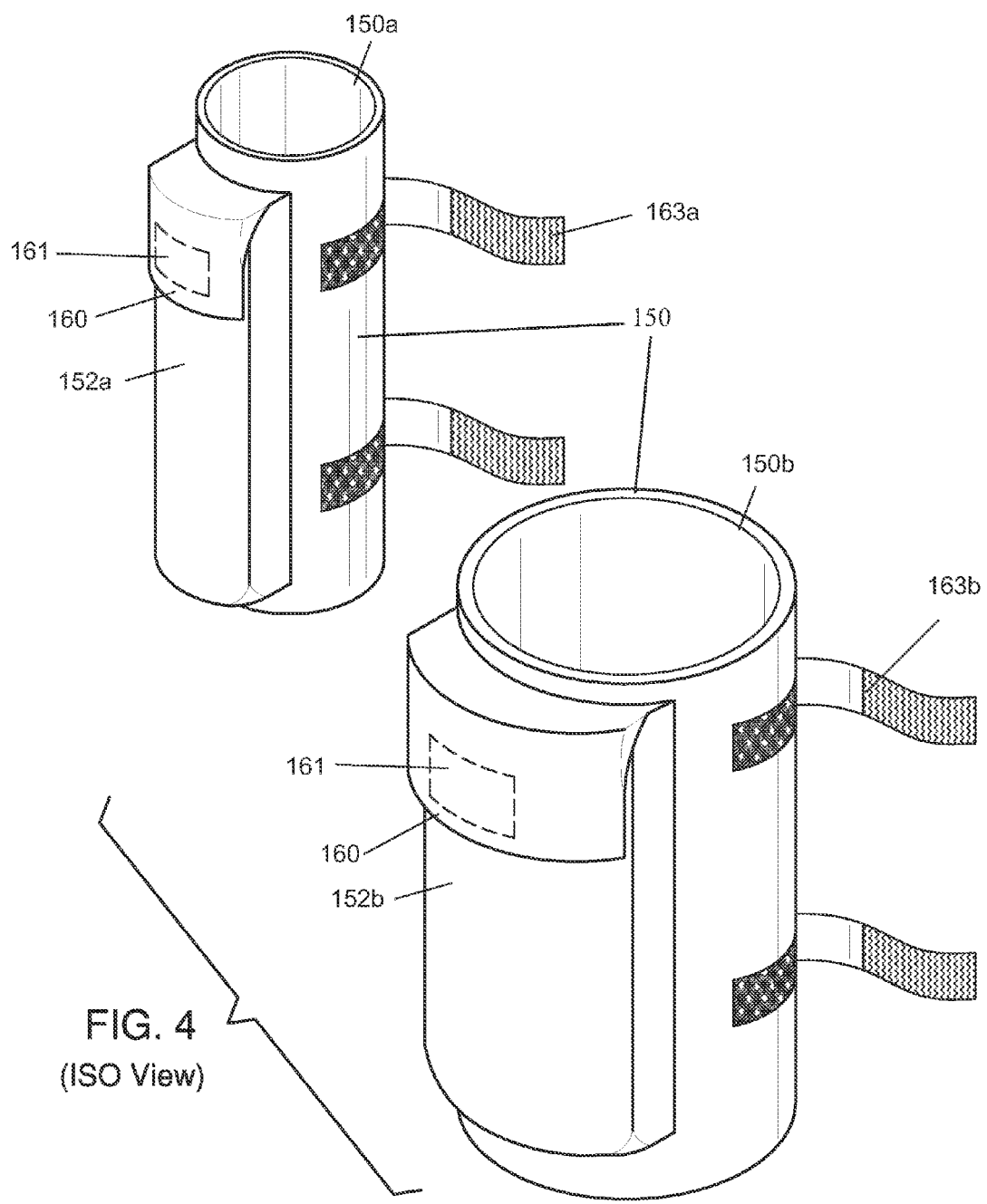
FIG. 4 shows an extremity tube for wearing around a person's limb. In some embodiments, the extremity tube can be tightened around the person's limb with the use of a hook-and-loop as shown. The extremity tube may come in two sizes, a larger one for wearing on the leg (e.g., thigh), and a smaller one for wearing around the arm or calf.
Figure 5:
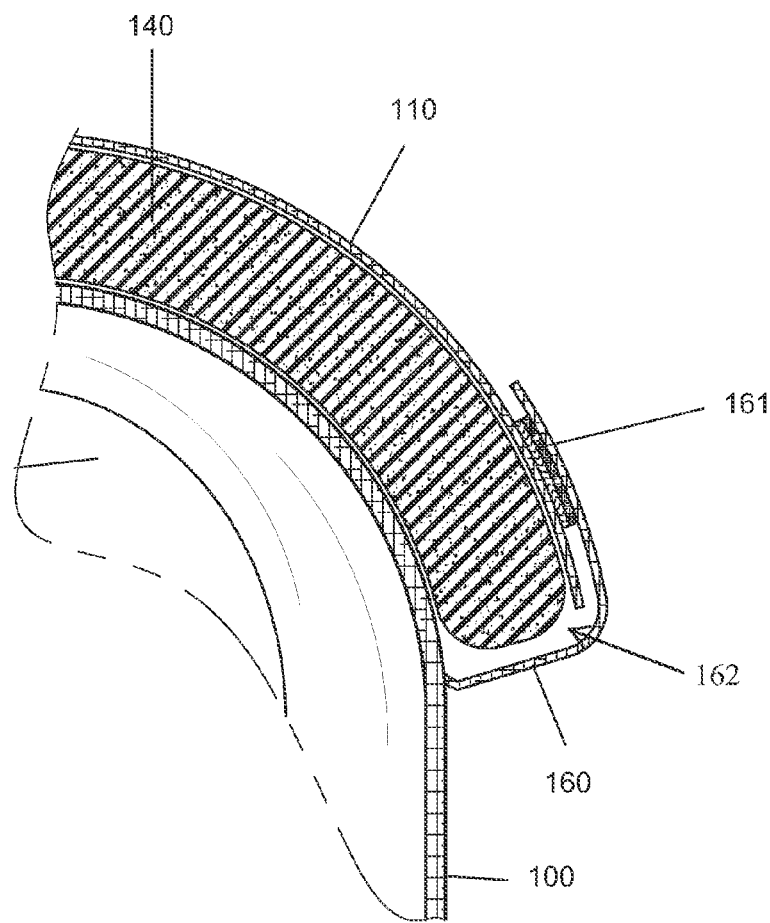
FIG. 5 shows a cross-sectional view of FIG. 1, wherein the heat/cold pack is inserted into the shoulder pocket.
Figure 6:
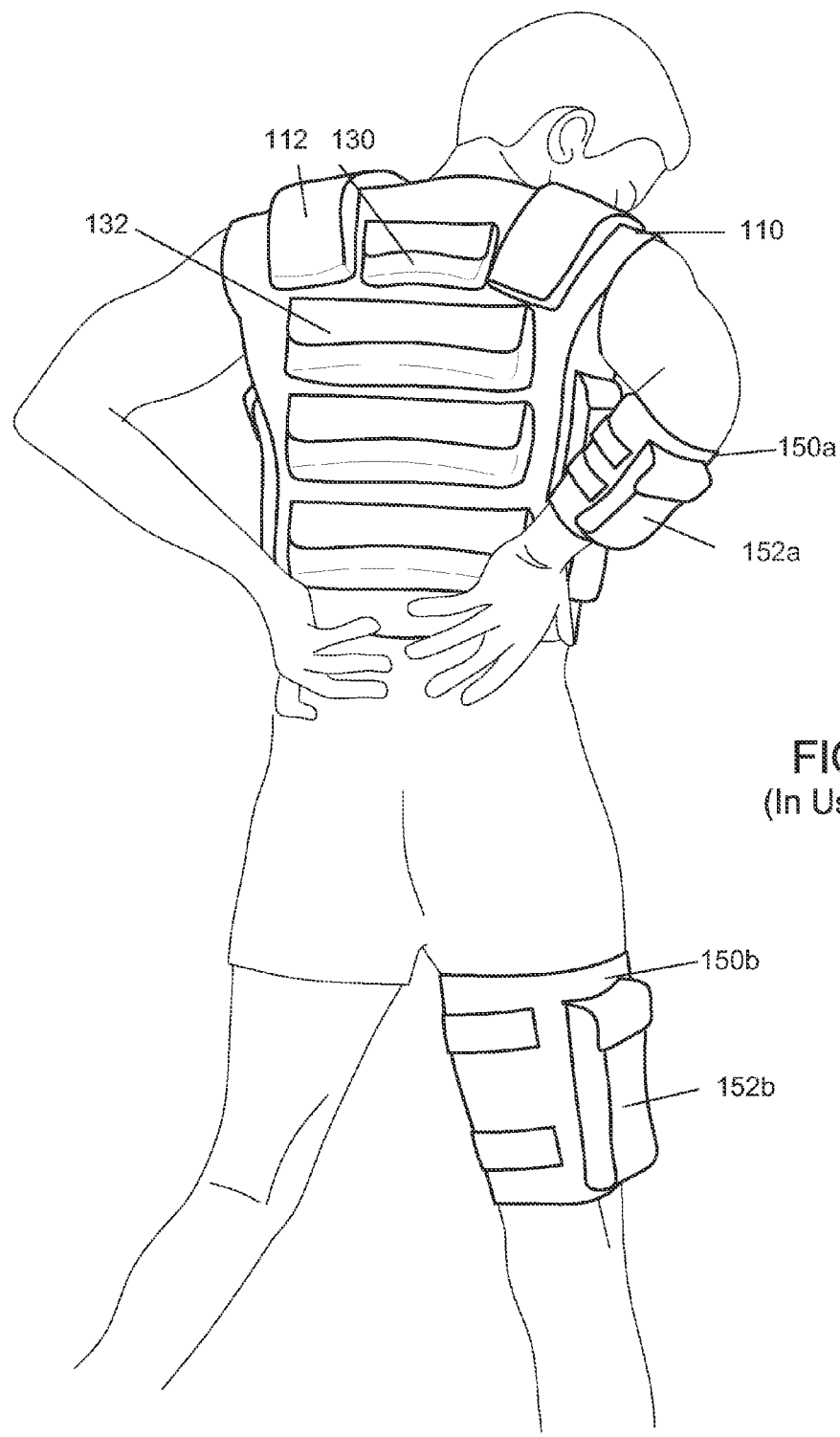
FIG. 6 shows an in-use view of the vest system.

Referring now to FIGS. 1-6, the present invention features a therapy vest system 10 for providing targeted heat or cold application to a person. In some embodiments, the vest 100 of the vest system 10 comprises a first shoulder pocket 110 secured over a first shoulder region of the vest, and also a second shoulder pocket 112 secured over a second shoulder region of the vest.

In some embodiments, the vest further comprises a first side pocket 120 secured to a first rib side region of the vest and also a second side pocket 122 secured to a second rib side region of the vest. The first side pocket 120 and second side pocket 122 can stretch from under the armpit to the waist line of the wearer. The vest contains an opening 104 which can be closed up with a hook-and-loop mechanism 105.

In some embodiments, the vest 100 further comprises a first back pocket 130 secured to a region matching a region between shoulder blades of the person wearing the vest. In some embodiments, the vest 100 further comprises a second back pocket 132, a third back pocket 134 and a fourth back pocket 136 serially secured to a region below that of the first pocket and matching to the back of the person.

For each pocket, a heating pack or a cooling pack 140 can be inserted therein for providing a targeted heating or cooling treatment to the person.

In some embodiments, the second, third and fourth pockets are about the same size, so that, for example a single sized heating or cooling pack can fit in any of these pockets. In some embodiments, the shoulder and side pockets are about the same size, so that, for example a single sized heating or cooling pack can fit in any of these pockets. In some embodiments, the vest system of the present invention comprises three different sized heating or cooling packs—one size for the first back pocket, one size for the second/third/fourth back pocket, and one size for the shoulder and side pockets.

The vest is constructed from a material that allows for the heating or the cooling pack to transmit heat or coolness, respectively, through to the person wearing the vest.

In some embodiments, the vest system comprises an extremity tube 150. The extremity tube 150 consists of an arm tube 150a and a leg tube 150b, wherein an extremity pocket 152a is secured to the arm tube 150a and an extremity pocket 152b is secured to the leg tube 150b. A person can insert a limb through an extremity tube and have the heat or coolness applied thereto. A plural of nylon loop fastener 163a are disposed on an exterior side of arm tube 150a and a plural of nylon loop fastener 163b are disposed on an exterior side of leg tube 150b.

In some embodiments, a flap 160 flaps over an opening 162 of one or more of the pockets to close off the pocket so that the heating or cooling pad 150 would not slide out of the pocket. The flaps can be closed up with a nylon loop fastener 161.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A therapy vest system (10) for providing targeted heat or cold application to a person for therapy purposes, the vest system (10) comprising a vest (100) which consists of:
   (a) an opening (104) on a front side of the vest (100) with plural fasteners (105);
   (b) a right shoulder pocket (110) secured over a right shoulder region of the vest (100);
   (c) a left shoulder pocket (112) secured over a left shoulder region of the vest (100);
   (d) a right side pocket (120) secured to a right rib side region of the vest (100);
   (e) a left side pocket (122) secured to a left rib side region of the vest (100);
   (f) a first back pocket (130) secured to a region of the vest (100) matching the region between the shoulder blades of the person;

(g) a second back pocket (132), a third back pocket (134) and a fourth back pocket (136) serially secured to a region of the vest (100) below that of the first back pocket (130) and matching to the back of the person;
wherein a heating pack or a cooling pack (140) is inserted into one or more of said right shoulder pocket (110), said left shoulder pocket (112), said right side pocket (120), said left side pocket (122), said first back pocket (130), said second back pocket (132), said third back pocket (134), and said fourth back pocket (136) for providing a targeted heating or cooling treatment to the person; wherein a flap (160) flaps over an opening (162) of the one or more said right shoulder pocket (110), said left shoulder pocket (112), said right side pocket (120), said left side pocket (122), said first back pocket (130), said second back pocket (132), said third back pocket (134), and said fourth back pocket (136) to close off the one or more said right shoulder pocket (110), said left shoulder pocket (112), said right side pocket (120), said left side pocket (122), said first back pocket (130), said second back pocket (132), said third back pocket (134), and said fourth back pocket (136); wherein the flap (160) is attached to the one or more said right shoulder pocket (110), said left shoulder pocket (112), said right side pocket (120), said left side pocket (122), said first back pocket (130), said second back pocket (132), said third back pocket (134), and said fourth back pocket (136) with a fastener (161); wherein said second, third and fourth back pockets (132, 134, 136) are the same size; wherein said right and left shoulder pockets (110, 112) and said right and left side pockets (120, 122) are the same size, and (h) an extremity tube (150) consisting of an arm tube (150*a*) and a leg tube (150*b*), wherein an extremity pocket (152*a*) is secured to said arm tube (150*a*) and an extremity pocket (152*b*) is secured to said leg tube (150*b*), wherein plural fasteners (163*a*) are disposed on an exterior side of said arm tube (150*a*) and plural fasteners (163*b*) are disposed on an exterior side of said leg tube (150*b*).

* * * * *